United States Patent [19]
Johnson et al.

[11] Patent Number: 5,769,959
[45] Date of Patent: Jun. 23, 1998

[54] PROCESS FOR REMOVING INSOLUABLE N-VINYL AMIDE POLYMER FROM EQUIPMENT

[75] Inventors: Thomas Albert Johnson, Orefield; Malee Leeaphon, Allentown, both of Pa.

[73] Assignee: Mitsubishi Chemical Corporation, Tokyo, Japan

[21] Appl. No.: 416,564

[22] Filed: Apr. 4, 1995

[51] Int. Cl.[6] ............................. B08B 3/08; B08B 9/00; B08B 9/08; C23D 17/00

[52] U.S. Cl. .................... 134/22.17; 134/22.19; 134/38; 134/42; 510/201; 510/202; 510/206; 510/212

[58] Field of Search ............... 134/2, 22.1, 22.17, 134/22.19, 38, 42; 252/548, 544, 153; 510/201, 202, 206, 212

[56] References Cited

U.S. PATENT DOCUMENTS

| | | | |
|---|---|---|---|
| 3,865,628 | 2/1975 | Callahan et al. | 134/2 |
| 4,490,557 | 12/1984 | Dawson et al. | 564/159 |
| 4,591,391 | 5/1986 | Shimizu et al. | 134/22.17 |
| 4,592,787 | 6/1986 | Johnson | 134/38 |
| 4,814,505 | 3/1989 | Kroener et al. | 564/216 |
| 5,381,807 | 1/1995 | Lee | 134/2 |

FOREIGN PATENT DOCUMENTS

| | | |
|---|---|---|
| 60-199685 | 10/1985 | Japan . |
| 3-318209 | 2/1991 | Japan . |
| 7118333 | 9/1995 | Japan . |

OTHER PUBLICATIONS

James E. Banks,"A Programmed Introduction to Organic Chemistry" Naming Organic Compounds, Second Edition. W.B Saunders Company, 1976, pp. 216–220.

*Primary Examiner*—Zeinab El-Arini
*Attorney, Agent, or Firm*—Ratner & Prestia

[57] ABSTRACT

Insoluble polymer formed during the distillation of N-vinylformamide is removed by contacting the insoluble polymer with an aqueous weakly basis solution in a closed system at elevated temperature. Polymer (up to 50 wt % polymer gel or 5.5 wt % dry polymer in reaction mixture) is treated with an aqueous solution of an amine, alkanolamine or weak inorganic base having a concentration of at least 1 molar. Solvents like alcohols, glycol ethers or amides may be added as a cosolvent in an amount of from 0 to about 85% by weight.

9 Claims, No Drawings

PROCESS FOR REMOVING INSOLUABLE N-VINYL AMIDE POLYMER FROM EQUIPMENT

TECHNICAL FIELD OF THE INVENTION

This invention relates to a process for the removal of insoluble N-vinyl amide polymer from process reaction and recovery equipment.

BACKGROUND OF THE INVENTION

Processes for the production of N-vinyl amides of the general structure:

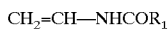

wherein $R_1$ is hydrogen, a $C_{1-6}$ alkyl group or a $C_{6-9}$ aryl or substituted aryl group are known. One method for forming these amides is by cracking carboxylic acid amides having the structure formula:

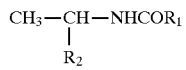

wherein $R_1$ is as described above, and $R_2$ is a $C_{1-9}$ alkoxy, carboxy, cyano or carboxamide group. Cracking is accomplished by heating the carboxylic acid amides to a temperature from about 210° to 400° C. in the presence of a catalyst. N-vinyl formamide (NVF), for example, is formed by the pyrolysis of N-(alkoxyalkyl)formamide; N-vinyl acetamide is formed by the pyrolysis of N-(alkoxyalkyl)acetamide. The reaction product obtained on thermal cracking of the respective N-(alkoxyalkyl)amide then is condensed and high purity N-vinyl amide recovered therefrom by fractional distillation.

Current industrial distillation processes are carried out to produce an NVF product containing from about 0.02 to 20% formamide. One of the problems associated with the recovery of N-vinyl formamide is that the high purity N-vinyl formamide monomer readily homopolymerizes in the reactor and recovery equipment. These homopolymerization products typically are NVF oligomers and polymers having a molecular weight as high as several hundred thousand. The resulting polymers, etc., are insoluble and adhere tenaciously to the reactor and distillation equipment surfaces. Over time, there is a buildup of insoluble byproduct which initially results in process inefficiencies. Eventually, there is plugging of the reactor and distillation equipment forcing a plant shutdown.

Removal of this polymer often requires time-consuming disassembly of distillation equipment to physically remove the polymer. If a packing has been used in the distillation column, it may have to be replaced or the polymer burned therefrom. As a result, the purity to which NVF monomer can be distilled is limited by the loss of distillation stages. Further, long periods of down-time are experienced for equipment cleanup.

Representative patents showing the preparation and recovery of N-vinyl amides are as follows:

U.S. Pat. No. 4,814,505 discloses a process for the distillation of reaction product obtained by the pyrolysis of formylalaninenitrile. The N-vinyl formamide is distilled at reduced pressure and low temperature. The patentees acknowledge the thermal sensitivity of N-vinyl formamide resulting in popcorn polymerization. Their solution for reducing polymerization in the recovery process resides in effecting distillation at reduced pressure and controlling the level of N-vinyl formamide in the distillate.

U.S. Pat. No. 4,490,557 discloses the preparation of ethylidene bisformamide and the synthesis of N-vinyl formamide therefrom by pyrolysis. A gaseous pyrolysis product is condensed and then distilled in a Vigreaux distillation column.

Japanese Application 60-199685 discloses a process for the production of N-vinyl formamide by the cracking of N-(α-hydroxyethyl)formamide. The patentees point out that large quantities of resins are produced as byproducts during the thermal decomposition of N-(α-hydroxyethyl)formamide which cause operational problems within the interior of reactor tubes and heat exchanger equipment. Their solution to reducing the quantity of byproduct resin resides in initially reacting the N-(α-hydroxyethyl)formamide with a polyhydric alcohol thereby forming an ether. In the subsequent distillation process, water distills first, then excess polyhydric alcohol, and, lastly, N-vinyl formamide with the polyhydric alcohol.

Japanese Application 3-318209 discloses several techniques for the prevention of self polymerization of NVF during distillation. One method contemplates reducing the pH of the reaction product prior to distillation. Another method contemplates subjecting the reaction product to a catalysis treatment using a weakly acidic, cation-exchanged resin prior to distillation. The patentees acknowledge problems existed with both methods, the first resulting from salt build-up and the second requiring substantial treatment time. To overcome those problems, the inventors suggested distilling off an NVF fraction in a thin film evaporator at reduced pressure. The unevaporated components then are removed from the system and the distillate super fractionated in the absence of these lower volatile components.

SUMMARY OF THE INVENTION

This invention relates to an improved process for the removal of insoluble polymer formed by the polymerization of an N-vinyl amide from N-vinyl amide production equipment. Polymer which forms during N-vinyl amide, and particularly N-vinyl formamide synthesis and distillation, is solubilized by contacting the polymer with a weak aqueous base solution at elevated temperature. In general, the bases used should have a $pK_b$ of from about 3.0 to 9.5 as measured in 0.01 to 0.1M aqueous solutions. Polymer (up to 50 wt % polymer gel or 5.5 wt % dry polymer in the reaction mixture) is solubilized by contacting the polymer with an aqueous solution of ammonia or an amine, e.g., methylamine or ethylamine, or aqueous carbonate, bicarbonate or phosphate, optionally mixed with a cosolvent for a time sufficient to effect dissolution.

There are several advantages associated with this invention and these include:

an ability to remove insoluble polymer buildup associated with the production of N-vinyl amides and from the distillation and other recovery equipment used to produce N-vinyl amides;

an ability to remove insoluble polymer buildup without physically dismantling reaction and distillation equipment; and/or an ability to remove insoluble polymer buildup within short periods of time thereby reducing production downtime.

DETAILED DESCRIPTION OF THE INVENTION

Insoluble polymer which forms during the synthesis, and particularly during the distillation of N-vinyl amides, e.g., NVF, to produce high purity NVF builds-up over time in the reaction and distillation equipment. Removal of the polymer from the equipment surfaces can be effected by contacting the polymer with a weakly basic, aqueous solution alone or in combination with a cosolvent at elevated temperature. The bases used should have a $pK_b$ of from about 3.0 to 9.5 as measured in 0.01 to 0.1M aqueous solutions.

The weak bases which can be used to form aqueous solutions and are sufficiently effective for dissolving the polymer include aqueous solutions of ammonia, $C_{1-8}$ alkyl amines such as mono-, di- and trimethylamines, mono-, di- and triethylamine, $C_2-C_6$ alkanolamines or $C_5-C_9$ heterocycles. Longer-chain mono-, di- and trialkylamines, such as isopropylamine, as well as aromatic amines, and alkanolamines may be used provided they are soluble in water, e.g., 15 g/100 g water. Weak inorganic bases such as alkali or alkaline earth metal carbonates, bicarbonates, borates, phenolates, phosphates (mono- and dibasic) are also effective in dissolving the polymer. Preferred alkali metals are sodium, potassium, and lithium.

The weakly basic aqueous solution used to dissolve the polymer should contain at least about 1 molar ammonia, alkylamine, amine derivative, or weak inorganic or organic base as described in order to effect dissolution of the polymer within commercially acceptable times. Concentrations above 1 molar, e.g., 1.5–3 molar, may be used to dissolve polymer within about 3 hours, at dissolution temperatures of about 110°–170° C., preferably 140° to 160° C. At lower temperatures, or lower concentrations, longer reaction times may be required.

Other conventional solvents, e.g., methanol, glycols, polyols, polyethers and/or dimethylformamide can also be added (up to about 85 wt % of the total mixture) as a cosolvent, to aid in the dissolution of the polymer. The solvent generally is added to the solution before the mixture is heated. Other alcohols or amides may also be used provided they are miscible at the reaction temperature. Generally, less than 85% by weight of the dispersion and preferably less than 50% by weight is cosolvent, no real advantages being observed.

The following examples are provided to illustrate various embodiments of the invention and are not intended to restrict the scope thereof.

EXAMPLE 1

Solubilization Tests

A series of tests were carried out to determine the effectiveness of various solvents as candidates for the dissolution of NVF polymer. The solvents and dissolution conditions are set forth in Table 1.

TABLE 1

NVF Polymer Dissolution Tests

| Run | Solvent | Temp. °C. | Time (hr) | Polymer Wt % | Result | $pK_b$ |
|---|---|---|---|---|---|---|
| 1 | 2.9M $NH_3$ in $H_2O$ | 110 | 23 | 10 gel | Polymer dissolved | 4.75 |
| 2 | 0.5M $NH_3$ in $H_2O$ | 150 | 6 | 10 gel | Polymer was not solubilized | 4.75 |
| 3 | 2.0M $NH_3$ in $H_2O$ | 160 | 2 | 10 gel | Polymer dissolved | 4.75 |
| 4 | 1.3M $DEA^1$ in MeOH | 150 | 3 | 10 gel | Polymer did not dissolve | 3.02 |
| 5 | 1.2M $MMA^2$ in $H_2O$ | 150 | 3 | 10 gel | Polymer dissolved | 3.36 |
| 6 | 1.2M $DMA^3$ in $H_2O$ | 150 | 3 | 10 gel | Polymer dissolved | 3.28 |
| 7 | 1.2M $MEA^4$ in $H_2O$ | 150 | 3 | 10 gel | Polymer dissolved | 3.25 |
| 8 | 1.8M DEA in $H_2O$ | 150 | 3 | 10 gel | Polymer dissolved | 3.02 |
| 9 | 1.2M $TMA^5$ in $H_2O$ | 150 | 3 | 10 gel | Polymer dissolved | 4.26 |
| 10 | DEA neat | 150 | 3 | 2.5 dry | Polymer did not dissolve | 3.02 |
| 11 | 3.5M $NH_3$ in $H_2O$ | 150 | 3 | 5.5 dry | Polymer dissolved | 4.75 |
| 12 | 1.6M DEA in $MeOH^6$ | 150 | 3 | 2 dry | Polymer did not dissolve | 3.02 |
| 13 | 1.2M $NH_3$ in 5% $H_2O$/86% MeOH | 150 | 4 | 10 gel | Polymer dissolved | 4.75 |
| 14 | 1.2M NaOH in $H_2O$ | 150 | 3 | 3 dry | Polymer did not dissolve | <<1 |
| 15 | 1.2M benzyltrimethylammonium hydroxide | 150 | 3 | 10 gel | Polymer did not dissolve | <<1 |
| 16 | 1.2M formic acid in $H_2O$ | 150 | 6 | 10 gel | Polymer did not dissolve | 10.25 |
| 17 | 1.2 $NH_3$ in $H_2O$ | 140 | 8 | 10 gel | Polymer dissolved | 4.75 |
| 18 | 2.8M $TEA^7$ in $H_2O$ | 150 | 5 | 10 gel | Polymer partially dissolved | 3.24 |
| 19 | $H_2O$ Neat | 150 | 3 | 10 gel | Polymer did not dissolve | — |
| 20 | 2.0M DEA in $DMF^8$ | 150 | 3 | 10 gel | Polymer did not dissolve | 3.02 |
| 21 | 4.2M 2-aminoethanol in $H_2O$ | 150 | 3 | 9 gel | Polymer solubilized | 4.56 |
| 22 | 2.0M $Na_2HPO_4$ in $H_2O$ | 150 | 3 | 8 gel | Polymer solubilized | 6.79 |
| 23 | 5.0M pyridine in $H_2O$ | 150 | 6 | 6.9 gel | Polymer solubilized | 8.77 |
| 24 | 4.7M aniline in $H_2O$ | 150 | 9.5 | 6.7 gel | Polymer partially dissolved | 9.42 |
| 25 | 2.0M $KHCO_3$ in $H_2O$ | 150 | 6 | 11 gel | Polymer solubilized | 3.75 |
| 26 | 2.0M $K_2CO_3$ in $H_2O$ | 150 | 3 | 8 gel | Polymer solubilized | 7.63 |
| 27 | 2.0M $Na_3PO_4.12H_2O$ in $H_2O$ | 150 | 4 | 6.3 gel | Polymer did not dissolve | 1.33 |
| 28 | 2.0M $Na_2B_4O_7.10H_2O$ in $H_2O$ | 150 | 3 | 8.6 gel | Polymer solubilized | 7.66 |

[1]DEA refers to diethylamine
[2]MMA refers to monomethylamine
[3]DMA refers to dimethylamine
[4]MEA refers to monoethylamine
[5]TMA refers to trimethylamine
[6]MeOH refers to methanol
[7]TEA refers to triethylamine
[8]DMF refers to dimethylformamide Table 1 shows that concentrated ammonia solutions, Run 1, 3 and 11, were effective in dissolving polymers within a 3 to 4 hour period at 150° C. and in 23 hours at 110° C. Low temperatures adversely affected solubilization rate (Run 1). Run 2, which used a low concentration of ammonia (0.5M), did not solubilize the polymer within 6 hours, but at a concentration of about 1M solubilization occurred within 8 hours (Run 17).

Runs 4, 10, 12, and 20, when compared to Run 8, show the importance of water in effecting dissolution of the polymer. However, water alone (Run 19) is not effective for solubilizing the polymer. Treatment with triethylamine (Run 18 at 27 wt % or 2.8 molar aqueous TEA) yielded partial solubility at 150° C. for 3 hours. The limited solubility of TEA in water and short reaction time may account for the poor results.

Runs 14–16 ($pK_b$ of <<1 and >10) show the ineffectiveness of strong bases and acids in effecting dissolution. For example, contacting the polymer with 5 to 6 wt % caustic (1 to 1.5 molar) at 100° C. (atmospheric pressure) for 8 hours did not solubilize the polymer (not reported in Table I), nor did caustic hydrolysis at 150° C. (80 psig) for 3 hours (Note run 14). Benzyltrimethylammonium hydroxide (an aqueous solution having 20.8 wt % benzyltrimethylammonium hydroxide or 1.2 molar) was tested with unsuccessful results (Note run 15). Formic acid also was tested with unsuccessful results. Up to 18.5 wt % (4 molar) formic acid was tested at a reaction temperature of 100° C. for 5.5 hours, and 5.0 wt % (1 molar) formic acid at 150° C. for 3 hours (Note run 16).

Runs 22, 25, and 26 show that the weak inorganic bases disodium hydrogen phosphate, potassium bicarbonate and potassium carbonate were effective in dissolving polymers within the same time period as for amines.

In conclusion, Runs 1, 3, 5, 6, 7, 8, 9, 11, 13, 17, 21, 22, 23, 25, 26, and 28 show that bases with a $pK_b$ of about 3 to 9.5, and preferably of molar concentrations greater than 1, whether organic or inorganic in nature, in the presence of water and over a sufficient time at temperature, 110° to 150° C., solubilize the polymer. When the $pK_b$ is too high (Run 24) or too low (Runs 14, 15 and 27) the aqueous base fails to solubilize the polymer.

Although not shown in Table 1, common solvents, e.g., alcohols, ketones, amides, ethers, esters, organic acids, nitrites, sulfoxides, sulfones, lactams, lactones, water, aqueous acids (organic or inorganic), aqueous alkali and alkaline earth hydroxides, anhydrous amines of all types, all fail to dissolve this polymer.

EXAMPLE 2

Stainless steel structured packing obtained from an NVF distillation column, was contaminated with a water insoluble NVF homopolymer gel (2.0 g). The gel was removed by removing a portion of the polymer from the packing and placing it in a 100 ml Parr stirred autoclave along with water (15 g) and 30% aqueous ammonia solution (2.5 ml). The ammonia concentration was about 2.0M and the polymer concentration about 10 wt %. The autoclave was sealed and the contents stirred and heated to 160° C. The pressure was increased to 120 psig. After 2 hours at 160° C., the autoclave was cooled to room temperature and opened. A yellow solution free of solids was observed. The insoluble polymeric material had completely dissolved from the stainless steel packing. The results are described as Run 3 in Table 1.

What is claimed is:

1. In a process for removing N-vinylformamide homopolymer buildup from process equipment wherein the N-vinylformamide homopolymer is contacted with a solvent under conditions sufficient to effect dissolution of such N-vinylformamide homopolymer, the improvement which comprises utilizing an aqueous solution of a weak base as said solvent, wherein the weak base is present in said aqueous solution in an amount from about 1 to 5 molar and the base has a $pK_b$ of from 3 to 9.5.

2. The process of claim 1 wherein the weak base is selected from the group consisting of ammonia, an amine, carbonate, bicarbonate, borate, phenolate or phosphate.

3. The process of claim 2 wherein the weak base is a $C_1$–$C_8$ alkyl amine or a $C_2$–$C_6$ alkanolamine or a $C_5$–$C_9$ heterocyclic, aromatic amine or ammonia.

4. The process of claim 2 wherein the weak base is an alkali or alkaline earth metal carbonate, bicarbonate, phosphate or borate.

5. The process of claim 2 wherein the polymer is contacted with said solvent at a temperature of from about 120°–160° C.

6. The process of claim 5 wherein the polymer is contacted with said solvent for a time from about 1 to 40 hours.

7. The process of claim 6 wherein a cosolvent selected from the group consisting of methanol and dimethylformamide is added to the weak base to enhance dissolution of the polymer.

8. The process of claim 7 wherein the cosolvent is present in an amount of up to about 85% weight.

9. The process of claim 5 wherein the amine is ammonia.

* * * * *

UNITED STATES PATENT AND TRADEMARK OFFICE
CERTIFICATE OF CORRECTION

PATENT NO. : 5,769,959
DATED : June 23, 1998
INVENTOR(S) : Thomas A. Johnson, et. al.

It is certified that error appears in the above-identified patent and that said Letters Patent is hereby corrected as shown below:

Title page, item [54] and col. 1, line 3, delete the word "INSOLUABLE" and substitute therefor --INSOLUBLE--.

Column 5, line 39, delete the word "nitrites" and substitute therefor --nitriles --.

Signed and Sealed this

Ninth Day of February, 1999

Attest:

Attesting Officer

*Acting Commissioner of Patents and Trademarks*